United States Patent
Powell et al.

(10) Patent No.: US 9,371,488 B2
(45) Date of Patent: Jun. 21, 2016

(54) BIOMASS PRETREATMENT FOR HYDROTHERMAL HYDROCATALYTIC CONVERSION

(71) Applicant: SHELL OIL COMPANY, Houston, TX (US)

(72) Inventors: Joseph Broun Powell, Houston, TX (US); Kimberly Ann Johnson, Richmond, TX (US)

(73) Assignee: Shell Oil Company, Houston, TX (US)

( * ) Notice: Subject to any disclaimer, the term of this patent is extended or adjusted under 35 U.S.C. 154(b) by 81 days.

(21) Appl. No.: 14/574,909

(22) Filed: Dec. 18, 2014

(65) Prior Publication Data
US 2015/0166898 A1 Jun. 18, 2015

Related U.S. Application Data

(60) Provisional application No. 61/917,429, filed on Dec. 18, 2013.

(51) Int. Cl.
| | | |
|---|---|---|
| C07C 1/00 | (2006.01) | |
| C07C 1/20 | (2006.01) | |
| C10G 1/00 | (2006.01) | |
| C10G 1/06 | (2006.01) | |
| C10L 1/04 | (2006.01) | |
| C07G 1/00 | (2011.01) | |
| C10G 3/00 | (2006.01) | |

(52) U.S. Cl.
CPC ........... *C10G 1/002* (2013.01); *C07G 1/00* (2013.01); *C10G 1/065* (2013.01); *C10G 3/44* (2013.01); *C10G 3/47* (2013.01); *C10G 3/48* (2013.01); *C10G 3/49* (2013.01); *C10G 3/50* (2013.01); *C10L 1/04* (2013.01); *C10G 2300/1014* (2013.01); *C10G 2300/4081* (2013.01); *C10G 2300/44* (2013.01); *C10L 2200/0469* (2013.01); *C10L 2290/06* (2013.01); *C10L 2290/08* (2013.01); *C10L 2290/10* (2013.01); *C12P 2201/00* (2013.01); *Y02P 30/20* (2015.11)

(58) Field of Classification Search
CPC .................................. C07C 1/00; C07C 1/20
USPC ................... 585/242, 240, 638, 310
See application file for complete search history.

(56) References Cited

U.S. PATENT DOCUMENTS

| | | |
|---|---|---|
| 2008/0300435 A1 | 12/2008 | Cortright et al. |
| 2010/0236988 A1 | 9/2010 | Gabrielov et al. |
| 2012/0151826 A1 | 6/2012 | Powell et al. |
| 2012/0156741 A1 | 6/2012 | Chedda et al. |
| 2012/0157730 A1 | 6/2012 | Powell et al. |
| 2012/0158836 A1 | 6/2012 | Bhogal et al. |
| 2012/0317872 A1 | 12/2012 | Powell et al. |
| 2012/0317873 A1 | 12/2012 | Johnson et al. |
| 2013/0109896 A1 | 5/2013 | Powell et al. |

(Continued)

OTHER PUBLICATIONS

Kölsch, P., et al.; "Ceramic Membranes for Water Separation from Organic Solvents"; Chem Eng. Technol.; vol. 25; pp. 357-363; 2002.

(Continued)

*Primary Examiner* — Thuan D Dang

(57) ABSTRACT

A method for thermo-catalytically producing $C_{4+}$ hydrocarbons from lignocellulosic biomass solids is provided by reducing the water content of the biomass feed prior to biomass hydrothermal hydrocatalytic conversion.

14 Claims, 3 Drawing Sheets

(56) References Cited

U.S. PATENT DOCUMENTS

| | | |
|---|---|---|
| 2013/0152457 A1 | 6/2013 | Powell et al. |
| 2013/0152458 A1 | 6/2013 | Powell et al. |
| 2014/0005444 A1 | 1/2014 | Komplin et al. |
| 2014/0005445 A1 | 1/2014 | Komplin et al. |
| 2014/0117275 A1 | 5/2014 | Powell et al. |
| 2014/0117276 A1 | 5/2014 | Powell et al. |
| 2014/0117277 A1 | 5/2014 | Powell et al. |
| 2014/0121418 A1 | 5/2014 | Powell et al. |
| 2014/0121419 A1 | 5/2014 | Powell et al. |
| 2014/0121420 A1 | 5/2014 | Powell et al. |
| 2014/0166221 A1 | 6/2014 | Powell et al. |
| 2014/0174432 A1 | 6/2014 | Powell |
| 2014/0174433 A1 | 6/2014 | Powell |

OTHER PUBLICATIONS

Hong-Jian Li, et al.; "Development and Characterization of Antifouling Cellulose Hollow Fiber UF Membranes for Oil-water Separation"; Journal of Membrane Science' vol. 279, Issue 1-2; pp. 328-335; 2006.

Urtiaga et al.; Separation and Purification Technology vol. 32, pp. 207-213; 2003.

Gayubo, et al.; "Kinetics, Catalysis, and Reaction Engineering" Ind. Eng. Chem. Res.; vol. 43, pp. 2610-2618; 2004.

International Search Report dated Jul. 1, 2015 of PCT/US2014/071030 filed Dec. 18, 2014.

BIOMASS PRETREATMENT FOR HYDROTHERMAL HYDROCATALYTIC CONVERSION

The present non-provisional application claims the benefit of U.S. Patent Application No. 61/917,429, filed Dec. 18, 2013, the entire disclosure of which are incorporated herein by reference.

FIELD OF THE INVENTION

The invention relates to pretreatment of biomass for the hydrothermal hydrocatalytic reactions in the production of $C_4+$ hydrocarbons suitable for use in preparation of transportation fuels and industrial chemicals from biomass. More specifically, the invention relates to reducing the water content of the biomass feed prior to biomass hydrothermal hydrocatalytic conversion.

BACKGROUND OF THE INVENTION

A significant amount of attention has been placed on developing new technologies for providing energy from resources other than fossil fuels. Biomass is a resource that shows promise as a fossil fuel alternative. As opposed to fossil fuel, biomass is also renewable.

Biomass may be useful as a source of renewable fuels. One type of biomass is plant biomass. Plant biomass is the most abundant source of carbohydrate in the world due to the lignocellulosic materials composing the cell walls in higher plants. Plant cell walls are divided into two sections, primary cell walls and secondary cell walls. The primary cell wall provides structure for expanding cells and is composed of three major polysaccharides (cellulose, pectin, and hemicellulose) and one group of glycoproteins. The secondary cell wall, which is produced after the cell has finished growing, also contains polysaccharides and is strengthened through polymeric lignin covalently cross-linked to hemicellulose. Hemicellulose and pectin are typically found in abundance, but cellulose is the predominant polysaccharide and the most abundant source of carbohydrates. However, production of fuel from cellulose poses a difficult technical problem. Some of the factors for this difficulty are the physical density of lignocelluloses (like wood) that can make penetration of the biomass structure of lignocelluloses with chemicals difficult and the chemical complexity of lignocelluloses that lead to difficulty in breaking down the long chain polymeric structure of cellulose into carbohydrates that can be used to produce fuel. Another factor for this difficulty is the nitrogen compounds and sulfur compounds contained in the biomass. The nitrogen and sulfur compounds contained in the biomass can poison catalysts used in subsequent processing.

Most transportation vehicles require high power density provided by internal combustion and/or propulsion engines. These engines require clean burning fuels which are generally in liquid form or, to a lesser extent, compressed gases. Liquid fuels are more portable due to their high energy density and their ability to be pumped, which makes handling easier.

Currently, bio-based feedstocks such as biomass provide the only renewable alternative for liquid transportation fuel. Unfortunately, the progress in developing new technologies for producing liquid biofuels has been slow in developing, especially for liquid fuel products that fit within the current infrastructure. Although a variety of fuels can be produced from biomass resources, such as ethanol, methanol, and vegetable oil, and gaseous fuels, such as hydrogen and methane, these fuels require either new distribution technologies and/or combustion technologies appropriate for their characteristics. The production of some of these fuels also tends to be expensive and raise questions with respect to their net carbon savings. There is a need to directly process biomass into liquid fuels, amenable to existing infrastructure.

Processing of biomass as feeds is challenged by the need to directly couple biomass hydrolysis to release sugars, and catalytic hydrogenation/hydrogenolysis/hydrodeoxygenation of the sugar, to prevent decomposition to heavy ends (caramel, or tars). Further, it is a challenge to minimize generation of waste products that may require treating before disposal and/or catalyst deactivation by poisons.

SUMMARY OF THE INVENTION

It is desirable to at least partially remove water from the biomass feed prior to carrying out catalytic hydrogenation/hydrogenolysis/hydrodeoxygenation of the biomass in a manner that does not reduce the effectiveness of the hydrothermal hydrocatalytic treatment while minimizing the amount of heat used in the process.

In one embodiment, a method is provided for thermocatalytically producing $C_{4+}$ hydrocarbons from lignocellulosic biomass solids comprising:

a. providing a wet cellulosic biomass solids containing at least 30 wt % water;

b. contacting the wet cellulosic biomass solids in a drying unit with a high boiling at least partially hydrophilic organic solvent, having a boiling point above 100° C. at atmospheric pressure, containing at least one of ethylene glycol, propylene glycol, tetrahydrofurfuryl alcohol, diols, monooxygenates greater than $C_4$, substituted phenol, or a mixture thereof and having a water content of less than 25 wt % water before said contact, at a temperature in the range of from 5° C. to 60° C. and a pressure in the range of from atmospheric pressure to 10,000 kPa producing a low water-content cellulosic biomass solids containing at most 25 wt % water and wet organic solvent;

c. contacting said low water-content lignocellulosic biomass solids in a hydrothermal digestion unit in the presence of a digestive solvent, hydrogen, and a catalyst capable of activating molecular hydrogen, thereby at least partially transforming said lignocellulosic biomass solids into a reaction product comprising one or more monooxygenates, glycols, diols, monooxygenates greater than C4, tetrahydrofurfuryl alcohol (THFA), and/or phenols in the liquor phase in the hydrothermal digestion unit and producing a product stream comprising the liquor phase and lignin residue;

d. flashing at least a portion of the product stream at a pressure of at most 5000 kPa and a temperature in the range of from 100° C. to 250° C. thereby separating a light monooxygenate stream and producing a heavy stream comprising glycols, diols, monooxygenates greater than C4, THFA, phenols and lignin residue;

e. separating a high boiling at least partially hydrophilic organic solvent stream from the heavy stream and recycling to the drying unit in step b;

f. removing at least a portion of water from the wet organic solvent producing a dried organic solvent;

g. recycling at least a portion of the dried organic solvent to the drying unit in step b as high boiling at least partially hydrophilic organic solvent;

h. contacting at least a portion of the light mono-oxygenate stream and/or at least a portion of the high boiling least partially hydrophilic organic solvent stream with a condensation catalyst to produce a condensation product stream containing ≥C4+ hydrocarbons.

The features and advantages of the invention will be apparent to those skilled in the art. While numerous changes may be made by those skilled in the art, such changes are within the spirit of the invention.

BRIEF DESCRIPTION OF THE DRAWINGS

The drawings illustrate certain aspects of some of the embodiments of the invention, and should not be used to limit or define the invention.

DETAILED DESCRIPTION OF THE INVENTION

Figure 1:
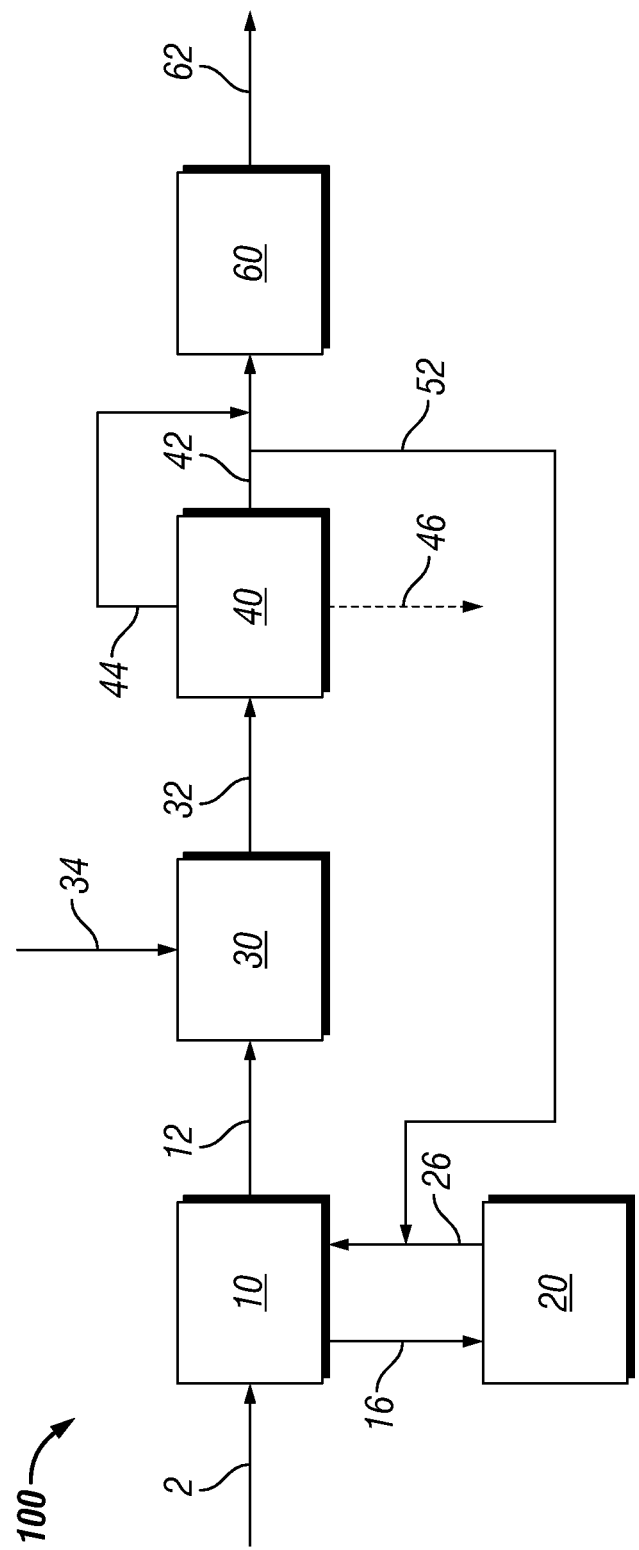
FIG. 1 is a schematically illustrated block flow diagram of an embodiment of a process 100 of this invention.

The invention relates to removal of water from the biomass feed prior to carry out catalytic hydrogenation/hydrogenolysis/hydrodeoxygenation of the biomass in a manner that does not reduce the effectiveness of the hydrothermal hydrocatalytic treatment by displacement of water from the biomass without shrinking pores.

In one embodiment, it has been found that, in conversion of biomass to liquid intermediates used to make biofuels via thermocatalytic conversion, water present in feed induces phase separations between oil, phenolic, and glycol components. Separation of water after aqueous phase reforming (APR) or hydrodoxygenation (HDO) reaction is inefficient due to formation of monooxygenate intermediates which partition into water and azeotrope when distilled. To avoid yield loss and high total organic carbon (TOC) loadings to the effluent water fed to a biotreater, these intermediates must be vaporized with water and passed over a condensation catalyst to make more lipophilic products which separate from water. Vaporization of the 50% water in feed is a substantial energy burden, and the excess water damages acid condensation catalyst. Pre-drying using solar drying (exposure to natural transpiration during storage), or using waste heat in a rotary drier, can lead to shrinkage of pores and loss of ability to dissolve the biomass in solvent at an acceptable rate. Any solvent used to dry the biomass without pore shrinkage comes in contact with the biomass, and is not readily separated from the process without use of excessive energy.

Any suitable (e.g., inexpensive and/or readily available) type of lignocellulosic biomass can be used. Suitable lignocellulosic biomass can be, for example, selected from, but not limited to, wood, forestry residues, agricultural residues, herbaceous material, municipal solid wastes, pulp and paper mill residues, and combinations thereof. Thus, in some embodiments, the biomass can comprise, for example, corn stover, straw, bagasse, miscanthus, sorghum residue, switch grass, duckweed, bamboo, water hyacinth, hardwood, hardwood chips, hardwood pulp, softwood, softwood chips, softwood pulp, and/or combination of these feedstocks. The biomass can be chosen based upon a consideration such as, but not limited to, cellulose and/or hemicelluloses content, lignin content, growing time/season, growing location/transportation cost, growing costs, harvesting costs and the like. Prior to treatment, the untreated biomass can be reduced in size (e.g., chopping, crushing or debarking) to a convenient size and certain quality that aids in moving the biomass or mixing and impregnating the chemicals from digestive solvent. Thus, in some embodiments, providing biomass can comprise harvesting a lignocelluloses-containing plant such as, for example, a hardwood or softwood tree. The tree can be subjected to debarking, chopping to wood chips of desirable thickness, and washing to remove any residual soil, dirt and the like.

The lignocellulosic biomass maybe washed to remove metal species and its corresponding anions such as Mg, Ca, Na, K Fe, Mn, Cl, $SO_4$, $PO_4$, $NO_3$ that are detrimental to catalysts or equipment used in the hydrothermal hydrocatalytic treatment of the biomass. Such wash methods are described in detail in commonly owned US patent applications filed on the same day.

A wet cellulosic biomass solids typically contains at least 30 wt % water, at least 35 wt % water, at least 40 wt % water, at least 45 wt % water, or even at least 50 wt % water, depending on the source of the cellulosic biomass solids.

The oxygenated hydrocarbons produced from the hydrothermal hydrocatalytic process are useful in the production of higher hydrocarbons suitable for use in transportation fuels and industrial chemicals from biomass. The higher hydrocarbons produced are useful in forming transportation fuels, such as synthetic gasoline, diesel fuel, and jet fuel, as well as industrial chemicals. As used herein, the term "higher hydrocarbons" refers to hydrocarbons having an oxygen to carbon ratio less than the oxygen to carbon ratio of at least one component of the biomass feedstock. As used herein the term "hydrocarbon" refers to an organic compound comprising primarily hydrogen and carbon atoms, which is also an unsubstituted hydrocarbon. In certain embodiments, the hydrocarbons of the invention also comprise heteroatoms (i.e., oxygen sulfur, phosphorus, or nitrogen) and thus the term "hydrocarbon" may also include substituted hydrocarbons. As used herein, the term "soluble carbohydrates" refers to monosaccharides or polysaccharides that become solubilized in a digestion process. Although the underlying chemistry is understood behind digesting cellulose and other complex carbohydrates and further transforming simple carbohydrates into organic compounds reminiscent of those present in fossil fuels, high-yield and energy-efficient digestion processes suitable for converting cellulosic biomass into fuel blends have yet to be developed. In this regard, the most basic requirement associated with converting cellulosic biomass into fuel blends using digestion and other processes is that the energy input needed to bring about the conversion should not be greater than the available energy output of the product fuel blends. Further the process should maximize product yield while minimizing char or tars. These basic requirements lead to a number of secondary issues that collectively present an immense engineering challenge that has not been solved heretofore.

Processing of biomass as feeds is challenged by the need to directly couple biomass hydrolysis to release sugars, and catalytic hydrogenation/hydrogenolysis/hydrodeoxygenation of the sugar, to prevent decomposition to heavy ends (caramel, char or tars). It has been found that it is desirable for the cellulosic biomass solids to contain at most 35 wt % water during the hydrothermal hydrocatalytic reaction (condensation reaction) to minimize energy requirements for further processing. Water in naturally occurring biomass may be typically present at 35 to 70 weight percent, most typically 45-55 weight percent. If fed to a hydrothermocatalytic digestion and reaction process, the biomass will be hydrolyzed to sugars, converted via hydrogen to sugar alcohols, when then under hydrogenolysis and hydrodeoxygenation to form monooxgenates such as ethanol, methanol, propanol, isopropanol, and the corresponding aldehydes and ketones. These monooxygenates for azeotropes with water, and are difficult to separate, requiring additional energy input and expensive equipment. By drying with a solvent mixture of at least partially hydrophilic organic solvent having a boiling point above 100° C. at atmospheric pressure such as diols and phenols also formed via these hydrogenolysis and HDO reactions, and via hydrolysis of lignin components present in biomass, azeotropes may be avoided, and a relatively clean water mixture with low concentrations of organic impurities may be separated by flash vaporization, for routing to a possible pretreatment wash step, and then to biotreatment. The use of the at least partially hydrophilic organic solvent having a boiling point above 100° C. at ambient temperature allows drying of the solvent by multieffect evaporation to reduce energy cost. In contrast, if significant concentrations (above 5 weight percent of monooxygenated alcohols and ketones of carbon number less than 4 are present, azeotropic mixtures can form, which are not readily separated by flash vaporization. Substantial yield loss of monooxygenates to water treatment is then realized.

In a conventional process water is not removed until after digestion and reaction, where all intermediates including water are sent to an acid condensation step and optional hydrotreating, after which water can be separated from largely de-oxygenated liquid fuel products. This requires contacting the acid condensation catalyst (e.g. ZSM-5) with relatively high concentrations of water, which can cause hydothermal damage. The current invention provides a means for drying biomass prior to hydrothermal digestion, to minimize formation of azeotropic compositions wherein organic intermediates are formed that are difficult to separate from water, such that water with organic intermediates must be routed together over acid condensation catalysts, resulting in hydrothermal damage.

In further embodiment, the invention relates to water removal by removing water with a high boiling at least partially hydrophilic organic solvent produced in the process (in situ generated solvent).

The invention process removes water from the biomass at relatively low temperatures to prevent yield loss to water soluble carbohydrates, acids, and other intermediates, while using in situ generated solvent to remove the water. The high boiling at least partially hydrophilic organic solvent has a boiling point above 100° C. at atmospheric pressure, preferably at least 10° C. higher than boiling point of water, more preferably at least 20° C. higher than boiling point of water, most preferably at least 30° C. higher than boiling point of water. The at least partially hydrophilic organic solvent has a percent saturation for water of at least 2.5 wt %, preferably at least 5 wt %, more preferably at least 10 wt %, most preferably at least 20 wt % at ambient temperature. The amount of water which can be dissolved in solvent at ambient temperature can be measured by Karl-Fischer titration after equilibrating with an excess amount of water, for example by shaking rigorously or stirring in a jar for a minimum of 30 minutes. Alternately, one can incrementally add water to dry solvent, to determine the point at which an immiscible phase is first observed, as evidenced by formation of turbidity after mixing.

In one embodiment of the process, the wet cellulosic biomass solids are contacted with a high boiling at least partially hydrophilic organic solvent (water-miscible or water-soluble) in a drying unit. The high boiling at least partially hydrophilic organic solvent may contain at least one of ethylene glycol, propylene glycol, diols, monooxygenates greater than $C_4$, tetrahydrofurfuryl alcohol, substituted phenol, and mixtures thereof. The high boiling at least partially hydrophilic organic solvent may contain diols having less than 6 carbon atoms and other organic compounds as long as they are miscible in the high boiling at least partially hydrophilic organic and meet the boiling point range. Diols include linear and cyclic diols of $C_2$-$C_6$ carbons including glycols ethylene glycol and 1,2-propylene glycol, and also butanediols, pentanediols, hexanediols, cyclopentanediols, methylcyclopentanediols, and cyclohexane diols. Heavy monooxygenates (greater than $C_4$) can include linear and cyclic $C_5$ and $C_6$ alcohols and ketones. The drying process is carried out in the range of from 10 kPa to 5000 kPa, preferably to 3000 kPa. The low water-content cellulosic biomass solids from the drying unit contains at most 25 wt % water, preferably at most 20 wt %, more preferably at most 15 wt %, and most preferably 10% wt % water based on the total amount of solid biomass feed to the digestion-reaction step. As a result, the vapor pressure of the hydrocatalytic digestion unit is at least 100 psi less than without water removal step.

In reference to FIG. 1, in one embodiment of the invention process 100, a wet cellulosic biomass solids 2 is introduced to a drying unit 10 with the high boiling at least partially hydrophilic organic solvent producing a low water-content cellulosic biomass solids 12 containing at most 25 wt % water and wet organic solvent 16. The term wet organic solvent is an organic solvent that contains more water content then the organic solvent before contact with the wet biomass solids. The wet biomass solids are contacted with the organic solvent at temperature in the range of from 5 to 60° C., preferably from 20° C. to 55° C. The low water-content lignocellulosic biomass solids 12 are contacted with hydrogen 34 in the presence of a catalyst capable of activating molecular hydrogen (hydrothermal hydrocatalytic catalyst), in a hydrothermal catalytic reaction zone 30 in the presence of a digestive solvent (such digestive solvent can at least in part be the high boiling at least partially hydrophilic organic solvent) thereby at least partially transforming said lignocellulosic biomass solids into a reaction product comprising one or more monooxygenates, glycols, diols, tetrahydrofurfuryl alcohol (THFA), and phenols in the liquor phase and producing a product stream 32 comprising the liquor phase and lignin residue. At least a portion of the product stream is flashed, in a separation step 40, at a pressure of at most 5000 kPa and a temperature in the range of 100° C. to 250° C. thereby separating a light mono-oxygenate stream 44 and producing a heavy stream 42 comprising glycols, THFA, diols, monooxygenates greater than $C_4$, phenols and lignin residue. The lignin residue 46 may be optionally removed from the product stream before or after removal of the light stream. A high boiling at least partially hydrophilic organic solvent stream 52 is separated from the heavy stream and recycled to the drying unit 10.

In a solvent drying step 20, at least a portion of water is removed from the wet organic solvent 16 producing a water stream (not shown) and a dried organic solvent 26 that is at least in part recycled to the drying unit 10 as high boiling at least partially hydrophilic organic solvent.

At least a portion of the light mono-oxygenate stream 44 and/or at least a portion of the high boiling least partially hydrophilic organic solvent stream 42 is contacted with a condensation catalyst, in a further processing step 60, to produce a condensation product stream 62 containing ≥$C_{4+}$ hydrocarbons.

Figure 2:
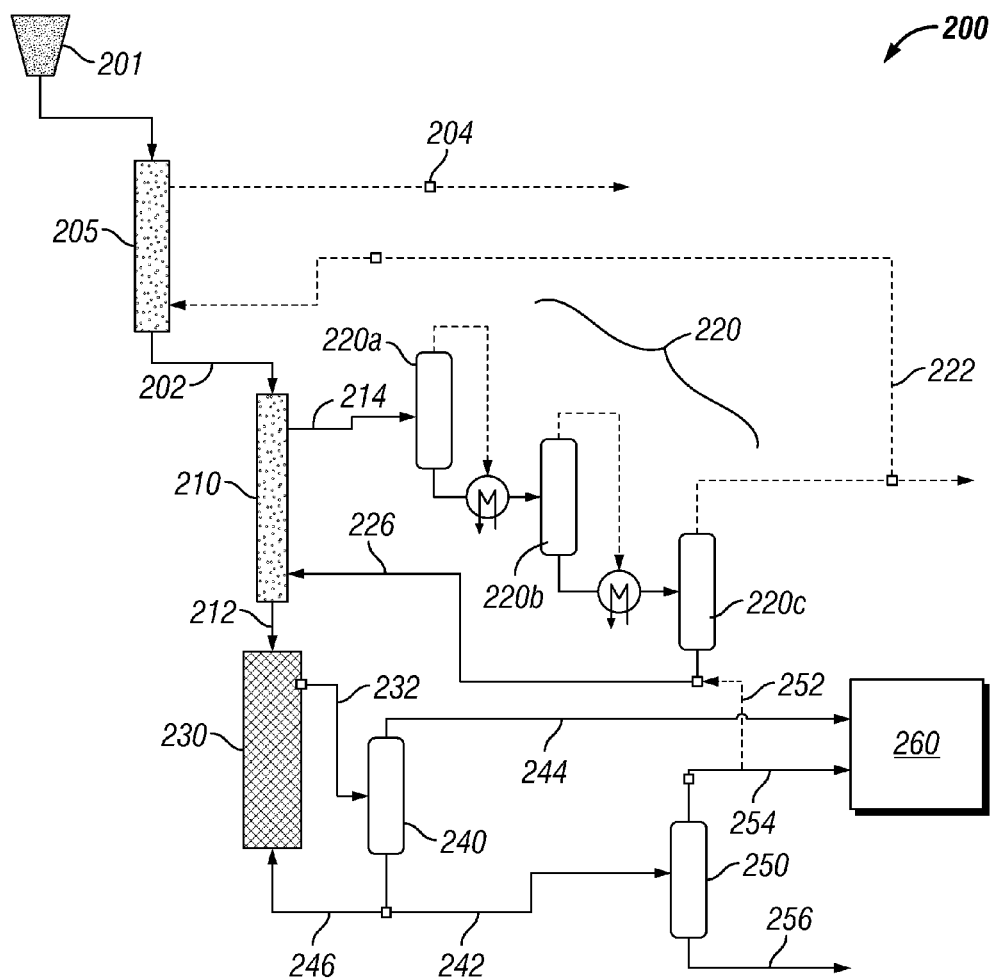
FIG. 2 is a schematically illustrated block flow diagram of another embodiment of a process 200 of this invention.

In reference to FIG. 2, in one embodiment of the invention process 200, a cellulosic biomass solids 201 is introduced to a pretreatment wash system 205 where the biomass is washed with an aqueous solution optionally containing weak acids at a temperature in the range from 0° C. to 60° C. that provides a wet biomass solids 202 with reduced amounts of metals and its ions compared to the biomass 201 and effluent 204. The wet biomass 202 is introduced to drying unit 210 with the high boiling at least partially hydrophilic organic solvent producing a low water-content cellulosic biomass solids 212 containing at most 25 wt % water and wet organic solvent 214. The term wet organic solvent is an organic solvent that contains more water content then the organic solvent before contact with the wet biomass solids. The wet biomass solids are contacted with the organic solvent at temperature in the range of from 5° C. to 60° C., preferably from 20° C. to 55° C. The low water-content lignocellulosic biomass solids 212 are contacted with hydrogen in the presence of a catalyst capable of activating molecular hydrogen (hydrothermal hydrocatalytic catalyst), in a hydrothermal catalytic reaction zone 230 in the presence of a digestive solvent (such digestive solvent can at least in part be the high boiling at least partially hydrophilic organic solvent) thereby at least partially transforming said lignocellulosic biomass solids into a reaction product comprising one or more monooxygenates, glycols, diols, monooxygenates greater than $C_4$, tetrahydrofurfuryl alcohol (THFA), and/or phenols in the liquor phase and producing a product stream 232 comprising the liquor phase and lignin residue. In one embodiment, at least a portion of the product stream is flashed, in a separation step 240, at a pressure of at most 5000 kPa and a temperature in the range of 100° C. to 250° C. thereby separating a light mono-oxygenate stream 244 and producing a heavy stream comprising glycols, diols, monooxygenates greater than $C_4$, THFA, phenols and lignin residue. The heavy stream may be in part recycled 246 to the hydrothermal catalytic reaction zone 230 as at least a portion of the digestive solvent. Lignin residue (may contain ash) may be optionally removed from the product stream before or after removal of the light stream or optionally before recycling to the hydrothermal catalytic reaction zone. In FIG. 2, lignin residue 256 is shown to be removed in a separation step 250 from the heavy stream 242 after removal of the light stream at 240 thereby producing a high boiling at least partially hydrophilic organic solvent stream 254 that may be recycled 252 to the drying unit 210.

In a solvent drying step 220, at least a portion of water is removed from the wet organic solvent via multieffect evaporator system 220a, 220b, 220c (shown in FIG. 2 with 3 vessels, however this number may vary from at least 2, from at least 3, and can be 4, 5, 6 or 8, or even as high as 10 vessels, or more depending on the efficiency of the effect and the amount of capital investment desired, to offset energy costs for drying the intermediate stream.) thereby producing a dried organic solvent 226 that is at least in part recycled to the drying unit 210 as high boiling at least partially hydrophilic organic solvent. The dotted line represents the overheaded steam vapor. In one embodiment, an exchanger optionally may be placed in front of the first evaporator (220a), where input steam for that step, to start the cascade. Then, 220b, 220c may take the overhead vapor from the previous step so as to not have to add any more steam. In the process of the invention, a steam heater may not be necessary for 214, however a steam heater may optionally be used.

Water removed from the multieffect evaporator system 220 may optionally be recycled 222 as at least a portion of the aqueous solution for the pretreatment wash system 205. The used wash water is discharged 204 from the pretreatment wash system for purification or disposal. In the system or process of the invention, the multieffect evaporator can be advantageously used to remove water from the product wet solvent 214 without additional or small amounts of heat input due to pressure in the drying process 210.

In another embodiment, vessel 205 can be the same as vessel 210 where the pretreatment wash and the multieffect drying with solvent is carried out in the same vessel. At least a portion of the light mono-oxygenate stream 244 and/or at least a portion of the high boiling at least partially hydrophilic organic solvent stream 244 is contacted with a condensation catalyst, in a further processing step 260, to produce a condensation product containing $\geq C_{4+}$ hydrocarbons.

Figure 3:
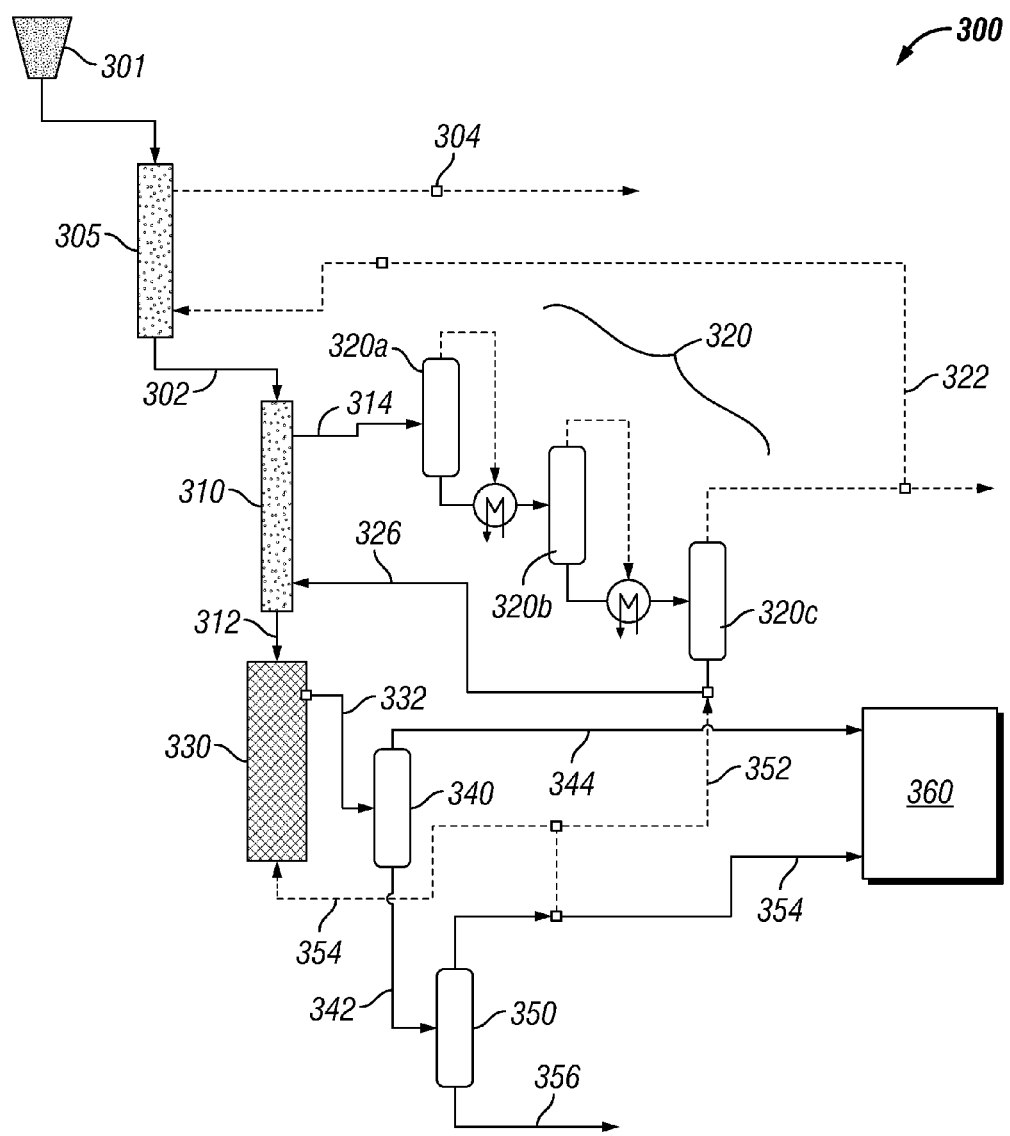
FIG. 3 is a schematically illustrated block flow diagram of another embodiment of a process 300 of this invention.

In reference to FIG. 3, in one embodiment of the invention process 300, a cellulosic biomass solids 301 is introduced to a pretreatment wash system 305 where the biomass is washed with an aqueous solution optionally containing weak acids at a temperature in the range from 0° C. to 60° C. that provides a wet biomass solids 302 with reduced amounts of metals and its ions compared to the biomass 301 and effluent 304. The wet biomass 302 is introduced to drying unit 310 with the high boiling at least partially hydrophilic organic solvent producing a low water-content cellulosic biomass solids 312 containing at most 25 wt % water and wet organic solvent 314. The term wet organic solvent is an organic solvent that contains more water content then the organic solvent before contact with the wet biomass solids. The wet biomass solids are contacted with the organic solvent at temperature in the range of from 5° C. to 60° C., preferably from 20° C. to 55° C. The low water-content lignocellulosic biomass solids 312 are contacted with hydrogen in the presence of a catalyst capable of activating molecular hydrogen (hydrothermal hydrocatalytic catalyst), in a hydrothermal catalytic reaction zone 330 in the presence of a digestive solvent (such digestive solvent can at least in part be the high boiling at least partially hydrophilic organic solvent) thereby at least partially transforming said lignocellulosic biomass solids into a reaction product comprising one or more monooxygenates, glycols, diols, tetrahydrofurfuryl alcohol (THFA), and/or phenols in the liquor phase and producing a product stream 332 comprising the liquor phase and lignin residue. In one embodiment, at least a portion of the product stream is flashed, in a separation step 340, at a pressure of at most 5000 kPa and temperature in the range of 100° C. to 250° C. thereby separating a light monooxygenate stream 344 and producing a heavy stream comprising glycols, diols, monooxygenates greater than $C_4$, THFA, phenols and lignin residue. In FIG. 3, lignin residue 356 is shown to be removed in a separation step 350 from the heavy stream 342 after removal of the light steam at 340 thereby producing a high boiling at least partially hydrophilic organic solvent stream 354 that may be recycled 352 to the drying unit 310. The high boiling at least partially hydrophilic organic solvent stream may be in part be recycled 354 to the hydrothermal catalytic reaction zone 330 as at least a portion of the digestive solvent.

In a solvent drying step 320, at least a portion of water is removed from the wet organic solvent via multieffect evaporator system 320a, 320b, 320c (shown in FIG. 3 with 3 vessels, however this number may vary from at least 2, from at least 3, and can be 4, 5, 6 or 8, or even as high as 10 vessels, or more depending on the efficiency of the effect and the amount of capital investment desired, to offset energy costs for drying the intermediate stream.) thereby producing a dried organic solvent 326 that is at least in part recycled to the drying unit 310 as high boiling at least partially hydrophilic organic solvent. The dotted line represents the overheaded steam vapor. In one embodiment, an exchanger optionally may be placed in front of the first evaporator (320a), where input steam for that step, to start the cascade. Then, 320b, 320c may take the overhead vapor from the previous step so as to not have to add any more steam. In the process of the invention, a steam heater may not be necessary for 314, however a steam heater may optionally be used.

Water removed from the multieffect evaporator system 320 may optionally be recycled 322 as at least a portion of the aqueous solution for the pretreatment wash system 305. The used wash water is discharged 304 from the pretreatment wash system for purification or disposal. In the system or process of the invention, the multieffect evaporator can be advantageously used to remove water from the product wet solvent 314 without additional or small amounts of heat input due to pressure in the drying process 310.

At least a portion of the light mono-oxygenate stream 344 and/or at least a portion of the high boiling at least partially hydrophilic organic solvent stream 344 is contacted with a condensation catalyst, in a further processing step 360, to produce a condensation product containing $\geq C_{4+}$ hydrocarbons.

In another embodiment, vessel 305 can be the same as vessel 310 where the pretreatment wash and the multieffect drying with solvent is carried out in the same vessel.

Water is difficult to remove in a hydrothermal hydrocatalytic process, because light monooxygenates are formed in the process which azeotrope with water during thermal separation, or cannot be readily removed by membranes. It is therefore necessary to send the water with monooxygenates to the condensation step to make lipophilic biofuels which then separate from water. But the large amount of water fed to condensation section stresses condensation catalyst such as ZSM-5 catalyst, shortening the condensation catalyst life.

The water fed to hydrothermal hydrocatalytic zone causes phase separation between glycol vs. phenolic and alkane intermediates. Formation of a second liquid phase leads to trapping of slurry catalyst, and difficulty in scale up of the digester reactors. Large concentrations of water are also the main contributor to pressure at digestion-reaction temperatures, and pressure for these large sized vessels.

It would be desirable to remove water prior to feeding the digester-reactor, to avoid these problems. However, thermal drying requires process energy (fuel fired with carbon intensity impact, or natural solar drying with time and logistics challenges). The pores of the biomass can collapse during thermal drying, such that time required for solvent digestion increases in the high pressure digesters. The process of the invention provides a process to effectively remove water from the process.

For example, in a process such as shown in FIG. 2 or FIG. 3, the high boiling at least partially hydrophilic organic solvent stream is provided to a low pressure drying column prior to feeding biomass to the digestion reaction zone 230 or 330. To illustrate, in one embodiment, the solvent is available at a higher pressure (in excess of 200 psi). By feeding at e.g. 150 psi, the water-miscible solvent can extract water from the biomass pores, and replace it with solvent. The pressure can be stepped down via the principles of multieffect evaporation (150, 100, 50 psig) such that steam produced overhead from the first effect can be used to heat and evaporate water in the next effect. This reduces the total amount of heat needed to evaporate water to 1/N where N is the number of effects (N=3 shown). The main source of process heat required to boil off water, is reduced by N. N can be a number in the range of 2 to 20 as discussed above. Since solvent is already available at pressure, mechanical recompression may not be required.

A multiple-effect evaporator is typically an apparatus for efficiently using the heat from steam to evaporate water. In a multiple-effect evaporator, water is boiled in a sequence of vessels, each held at a lower pressure than the last (described above as an example). Because the boiling temperature of water decreases as pressure decreases, the vapor boiled off in one vessel can be used to heat the next, and only the first vessel (at the highest pressure) requires an external source of heat or in the instant invention process using the pressure already exiting in the biomass drying step. Multi-effect evaporators are commonly used to evaporate water from salt solution such as in desalination plants and described in more detailed for example in J. M. Coulson and J. F. Richardson, Chemical Engineering, Vol. 2, pp. 791-805 (1955). Multieffect evaporators are also commercially available, for example, from GEA Process Engineering Inc., or the Andritz Group.

Vapor pressure in digestion reaction can be reduced by a substantial amount by the process of the invention. For example, compared to the free water phase that gives a vapor pressure of greater than 3500 kPa depending on temperature selected, to a water partial pressure that is less than 1000 kPa at the same temperature. In the invention process, typically, the vapor pressure of the digestion reaction (hydrocatalytic digestion unit) is at least 1000 kPa less, than without the water removal step, preferably at least 1500 kPa less, and most preferably 2000 kPa less.

Alternatively, the drying can be conducted by using water permeable membranes such as polymers and ceramics or by nanofiltration. For example, ceramic membranes as disclosed by Kölsch, P., Sziládi, M., Noack, M., Caro, J., Kotsis, L., Kotsis, I. and Sieber, I. (2002), Ceramic Membranes for Water Separation from Organic Solvents. Chem. Eng. Technol., 25: 357-363. As another example, polymer membranes such as a hydrophilic hollow fiber untrafiltration membrane made from a dope containing cellulose/monohydrate N-mehtylmorpholine-N-oxide/polyethylene glycol as disclosed by Hong-Jian Li, Yi-Ming Cao, Jian-Jun Qin, Xing-Ming Jie, Tong-Hua Wang, Jian-Hui Liu, Quan Yuan, Development and characterization of anti-fouling cellulose hollow fiber UF membranes for Oil-water separation. Journal of Membrane Science, volume 279, Issues 1-2, August 2006, Pages 328-335. Use of membranes allows water separations to occur with reduced energy input, relative to thermal drying. Pervaporation membranes may be employed, as described by Urtiaga et al. (Separation and Purification Technology 32 (2003) 207-213), or use of molecular sieve fixed bed driers.

For the hydrothermal catalytic reaction zone, the zone may have one or more vessels. In one embodiment in the digestion/reaction zone hydrolysis and hydrothermal hydrocatalytic reaction of the treated biomass is carried out in one or more vessels. These vessels may be digesters or reactors or combination thereof including a combination hydrothermal hydrocatalytic digestion unit In some embodiments, lignocellulosic biomass (solids) being continuously or semi-continuously added to the hydrothermal digestion unit or hydrothermal hydrocatalytic digestion unit may be pressurized before being added to the unit, particularly when the hydrothermal (hydrocatalytic) digestion unit is in a pressurized state. Pressurization of the cellulosic biomass solids from atmospheric pressure to a pressurized state may take place in one or more pressurization zones before addition of the cellulosic biomass solids to the hydrothermal (hydrocatalytic) digestion unit. Suitable pressurization zones that may be used for pressurizing and introducing lignocellulosic biomass to a pressurized hydrothermal digestion unit or hydrothermal hydrocatalytic digestion unit are described in more detail in commonly owned United States Patent Application Publications US20130152457 and US20130152458. Suitable pressurization zones described therein may include, for example, pressure vessels, pressurized screw feeders, and the like. In some embodiments, multiple pressurization zones may be connected in series to increase the pressure of the cellulosic biomass solids in a stepwise manner. The digestion and the hydrothermal hydrocatalytic reaction in the hydrothermal catalytic reaction zone (or digestion reaction zone) may be conducted separately, partially combined, or in situ.

In some embodiments, the digestion rate of cellulosic biomass solids may be accelerated in the presence of a liquid phase containing a digestion solvent. In some instances, the liquid phase may be maintained at elevated pressures that keep the digestion solvent in a liquid state when raised above its normal boiling point. Although the more rapid digestion rate of cellulosic biomass solids under elevated temperature and pressure conditions may be desirable from a throughput standpoint, soluble carbohydrates may be susceptible to degradation at elevated temperatures. One approach for addressing the degradation of soluble carbohydrates during hydrothermal digestion is to conduct an in situ catalytic reduction reaction process so as to convert the soluble carbohydrates into more stable compounds as soon as possible after their formation.

In certain embodiments, a slurry catalyst may be effectively distributed from the bottom of a charge of cellulosic biomass solids to the top using upwardly directed fluid flow to fluidize and upwardly convey slurry catalyst particulates into the interstitial spaces within the charge for adequate catalyst distribution within the digesting cellulosic biomass solids. Suitable techniques for using fluid flow to distribute a slurry catalyst within cellulosic biomass solids in such a manner are described in commonly owned United States Patent Application Publications US20140005445 and US20140005444. In addition to affecting distribution of the slurry catalyst, upwardly directed fluid flow may promote expansion of the cellulosic biomass solids and disfavor gravity-induced compaction that occurs during their addition and digestion, particularly as the digestion process proceeds and their structural integrity decreases. Methods of effectively distributing molecular hydrogen within cellulosic biomass solids during hydrothermal digestion is further described in commonly owned United States Patent Application Publications US20140174433 and US20140174432.

In another embodiment the hydrothermal hydrocatalytic digestion unit may be configured as disclosed in a co-pending United States Patent Application Publication US20140117276. In the digestion zone, the size-reduced biomass is contacted with the digestive solvent where the digestion reaction takes place. The digestive solvent must be effective to digest lignins.

In some embodiments, at least a portion of oxygenated hydrocarbons produced in the hydrothermal hydrocatalytic reaction zone such as the at least partially hydrophilic organic solvent are recycled within the process and system to at least in part from the in situ generated solvent, which is used in the biomass digestion process. Further, by controlling the degradation of carbohydrate in the hydrothermal hydrocatalytic reaction (e.g., hydrogenolysis process), hydrogenation reactions can be conducted along with the hydrogenolysis reaction at temperatures ranging from 150° C. to 300° C. As a result, a separate hydrogenation reaction section can optionally be avoided, and the fuel forming potential of the biomass feedstock fed to the process can be increased. Further, the removal of water in the drying step 10 or 210 or 310 allows for the vapor pressure of the hydrocatalytic digestion unit to be lower with less water being present, The process of claim vapor pressure of the hydrocatalytic digestion unit can be at least 100 psi less than without water removal step.

In various embodiments, the fluid phase digestion medium in which the hydrothermal digestion and catalytic reduction reaction, in the hydrothermal hydrocatalytic reaction zone, are conducted may comprise an organic solvent and water. Although any organic solvent that is at least partially miscible with water may be used as a digestion solvent, particularly advantageous organic solvents are those that can be directly converted into fuel blends and other materials without being separated from the alcoholic component being produced from the cellulosic biomass solids. That is, particularly advantageous organic solvents are those that may be co-processed along with the alcoholic component during downstream processing reactions into fuel blends and other materials. Suitable organic solvents in this regard may include, for example, ethylene glycol, propylene glycol, glycerol, phenolics and any combination thereof. In situ generated high boiling at least partially hydrophilic organic solvent stream are particularly desirable in this regard.

In some embodiments, catalysts capable of activating molecular hydrogen hydrothermal hydrocatalytic catalysts, which are capable of activating molecular hydrogen (e.g., hydrogenolysis catalyst) and conducting a catalytic reduction reaction may comprise a metal such as, for example, Cr, Mo, W, Re, Mn, Cu, Cd, Fe, Co, Ni, Pt, Pd, Rh, Ru, Ir, Os, and alloys or any combination thereof, either alone or with promoters such as Au, Ag, Cr, Zn, Mn, Sn, Bi, B, O, and alloys or any combination thereof. In some embodiments, the catalysts and promoters may allow for hydrogenation and hydrogenolysis reactions to occur at the same time or in succession of one another. In some embodiments, such catalysts may also comprise a carbonaceous pyropolymer catalyst containing transition metals (e.g., Cr, Mo, W, Re, Mn, Cu, and Cd) or Group VIII metals (e.g., Fe, Co, Ni, Pt, Pd, Rh, Ru, Ir, and Os). In some embodiments, the foregoing catalysts may be combined with an alkaline earth metal oxide or adhered to a catalytically active support. In some or other embodiments, the catalyst may be deposited on a catalyst support that may not itself be catalytically active.

In some embodiments, the hydrothermal hydrocatalytic catalyst may comprise a slurry catalyst. In some embodiments, the slurry catalyst may comprise a poison-tolerant catalyst. As used herein the term "poison-tolerant catalyst" refers to a catalyst that is capable of activating molecular hydrogen without needing to be regenerated or replaced due to low catalytic activity for at least 12 hours of continuous operation. Use of a poison-tolerant catalyst may be particularly desirable when reacting soluble carbohydrates derived from cellulosic biomass solids that have not had catalyst poisons removed therefrom. Catalysts that are not poison tolerant may also be used to achieve a similar result, but they may need to be regenerated or replaced more frequently than does a poison-tolerant catalyst.

In some embodiments, suitable poison-tolerant catalysts may include, for example, sulfided catalysts. In some or other embodiments, nitrided catalysts may be used as poison-tolerant catalysts. Sulfided catalysts suitable for activating molecular hydrogen and buffers suitable for use with such catalysts are described in commonly owned United States Patent Application Publications US20120317872, US20130109896, US20120317873, and US20140166221. Sulfiding may take place by treating the catalyst with hydrogen sulfide or an alternative sulfiding agent, optionally while the catalyst is disposed on a solid support. In more particular embodiments, the poison-tolerant catalyst may comprise (a) sulfur and (b) Mo or W and (c) Co and/or Ni or mixtures thereof. The pH buffering agent, may be suitable be an inorganic salt, particularly alkali salts such as, for example, potassium hydroxide, sodium hydroxide, and potassium carbonate or ammonia. In other embodiments, catalysts containing Pt or Pd may also be effective poison-tolerant catalysts for use in the techniques described herein. When mediating in situ catalytic reduction reaction processes, sulfided catalysts may be particularly well suited to form reaction products comprising a substantial fraction of glycols (e.g., $C_2$-$C_6$ glycols) without producing excessive amounts of the corresponding monohydric alcohols. Although poison-tolerant catalysts, particularly sulfided catalysts, may be well suited for forming glycols from soluble carbohydrates, it is to be recognized that other types of catalysts, which may not necessarily be poison-tolerant, may also be used to achieve a like result in alternative embodiments. As will be recognized by one having ordinary skill in the art, various reaction parameters (e.g., temperature, pressure, catalyst composition, introduction of other components, and the like) may be modified to favor the formation of a desired reaction product. Given the benefit of the present disclosure, one having ordinary skill in the art will be able to alter various reaction parameters to change the product distribution obtained from a particular catalyst and set of reactants.

In some embodiments, slurry catalysts suitable for use in the methods described herein may be sulfided by dispersing a slurry catalyst in a fluid phase and adding a sulfiding agent thereto. Suitable sulfiding agents may include, for example, organic sulfoxides (e.g., dimethyl sulfoxide), hydrogen sulfide, salts of hydrogen sulfide (e.g., NaSH), and the like. In some embodiments, the slurry catalyst may be concentrated in the fluid phase after sulfiding, and the concentrated slurry may then be distributed in the cellulosic biomass solids using fluid flow. Illustrative techniques for catalyst sulfiding that may be used in conjunction with the methods described herein are described in United States Patent Application Publication US20100236988.

In various embodiments, slurry catalysts used in conjunction with the methods described herein may have a particulate size of 250 microns or less. In some embodiments, the slurry catalyst may have a particulate size of 100 microns or less, or 10 microns or less. In some embodiments, the minimum particulate size of the slurry catalyst may be 1 micron. In some embodiments, the slurry catalyst may comprise catalyst fines in the processes described herein.

Catalysts that are not particularly poison-tolerant may also be used in conjunction with the techniques described herein. Such catalysts may include, for example, Ru, Pt, Pd, or compounds thereof disposed on a solid support such as, for example, Ru on titanium dioxide or Ru on carbon. Although such catalysts may not have particular poison tolerance, they may be regenerable, such as through exposure of the catalyst to water at elevated temperatures, which may be in either a subcritical state or a supercritical state.

In some embodiments, the catalysts used in conjunction with the processes described herein may be operable to generate molecular hydrogen. For example, in some embodiments, catalysts suitable for aqueous phase reforming (i.e., APR catalysts) may be used. Suitable APR catalysts may include, for example, catalysts comprising Pt, Pd, Ru, Ni, Co, or other Group VIII metals alloyed or modified with Re, Mo, Sn, or other metals such as described in United States Patent Application Publication US20080300435.

In some embodiments, the alcoholic component formed from the cellulosic biomass solids may be further reformed into a biofuel. Reforming the alcoholic component into a biofuel or other material may comprise any combination and sequence of further hydrogenolysis reactions and/or hydrogenation reactions, condensation reactions, isomerization reactions, oligomerization reactions, hydrotreating reactions, alkylation reactions, dehydration reactions, desulfurization reactions, and the like. The subsequent conversion reactions may be catalytic or non-catalytic. In some embodiments, an initial operation of downstream conversion may comprise a condensation reaction, often conducted in the presence of a condensation catalyst, in which the alcoholic component or a product derived therefrom is condensed with another molecule to form a higher molecular weight compound. As used herein, the term "condensation reaction" will refer to a chemical transformation in which two or more molecules are coupled with one another to form a carbon-carbon bond in a higher molecular weight compound, usually accompanied by the loss of a small molecule such as water or an alcohol. An illustrative condensation reaction is the Aldol condensation reaction, which will be familiar to one having ordinary skill in the art. Additional disclosure regarding condensation reactions and catalysts suitable for promoting condensation reactions is provided hereinbelow.

In some embodiments, methods described herein may further comprise performing a condensation reaction on the alcoholic component or a product derived therefrom. In various embodiments, the condensation reaction may take place at a temperature ranging between 5° C. and 500° C. The condensation reaction may take place in a condensed phase (e.g., a liquor phase) or in a vapor phase. For condensation reactions taking place in a vapor phase, the temperature may range between 75° C. and 500° C., or between 125° C. and 450° C. For condensation reactions taking place in a condensed phase, the temperature may range between 5° C. and 475° C., or between 15° C. and 300° C., or between 20° C. and 250° C.

ZSM5 is reversibly deactivated by coke formation which can be eliminated by combustion. But in the presence of steam, it undergoes a dealumination process that causes a permanent loss of acidity and a corresponding loss in activity. Higher steam partial pressure and or higher temperature conditions increase the rate of this deactivation. (Ind. Eng. Chem. Res. 2004, 43, 2610-2618).

Each reactor vessel preferably includes an inlet and an outlet adapted to remove the product stream from the vessel or reactor. In some embodiments, the vessel in which at least some digestion occurs may include additional outlets to allow for the removal of portions of the reactant stream. In some embodiments, the vessel in which at least some digestion occurs may include additional inlets to allow for additional solvents or additives.

In various embodiments, the higher molecular weight compound produced by the condensation reaction may comprise $\geq C_4$ hydrocarbons. In some or other embodiments, the higher molecular weight compound produced by the condensation reaction may comprise $\geq C_6$ hydrocarbons. In some embodiments, the higher molecular weight compound produced by the condensation reaction may comprise $C_4$-$C_{30}$ hydrocarbons. In some embodiments, the higher molecular weight compound produced by the condensation reaction may comprise $C_6$-$C_{30}$ hydrocarbons. In still other embodiments, the higher molecular weight compound produced by the condensation reaction may comprise $C_4$-$C_{24}$ hydrocarbons, or $C_6$-$C_{24}$ hydrocarbons, or $C_4$-$C_{18}$ hydrocarbons, or $C_6$-$C_{18}$ hydrocarbons, or $C_4$-$C_{12}$ hydrocarbons, or $C_6$-$C_{12}$ hydrocarbons. As used herein, the term "hydrocarbons" refers to compounds containing both carbon and hydrogen without reference to other elements that may be present. Thus, heteroatom-substituted compounds are also described herein by the term "hydrocarbons."

The particular composition of the higher molecular weight compound produced by the condensation reaction may vary depending on the catalyst(s) and temperatures used for both the catalytic reduction reaction and the condensation reaction, as well as other parameters such as pressure.

In some embodiments, a single catalyst may mediate the transformation of the alcoholic component into a form suitable for undergoing a condensation reaction as well as mediating the condensation reaction itself. In other embodiments, a first catalyst may be used to mediate the transformation of the alcoholic component into a form suitable for undergoing a condensation reaction, and a second catalyst may be used to mediate the condensation reaction. Unless otherwise specified, it is to be understood that reference herein to a condensation reaction and condensation catalyst refers to either type of condensation process. Further disclosure of suitable condensation catalysts now follows.

In some embodiments, a single catalyst may be used to form a higher molecular weight compound via a condensation reaction. Without being bound by any theory or mechanism, it is believed that such catalysts may mediate an initial dehydrogenation of the alcoholic component, followed by a condensation reaction of the dehydrogenated alcoholic component. Zeolite catalysts are one type of catalyst suitable for directly converting alcohols to condensation products in such a manner. A particularly suitable zeolite catalyst in this regard may be ZSM-5, although other zeolite catalysts may also be suitable.

In some embodiments, two catalysts may be used to form a higher molecular weight compound via a condensation reaction. Without being bound by any theory or mechanism, it is believed that the first catalyst may mediate an initial dehydrogenation of the alcoholic component, and the second catalyst may mediate a condensation reaction of the dehydrogenated alcoholic component. Like the single-catalyst embodiments discussed previously above, in some embodiments, zeolite catalysts may be used as either the first catalyst or the second catalyst. Again, a particularly suitable zeolite catalyst in this regard may be ZSM-5, although other zeolite catalysts may also be suitable.

Various catalytic processes may be used to form higher molecular weight compounds by a condensation reaction. In some embodiments, the catalyst used for mediating a condensation reaction may comprise a basic site, or both an acidic site and a basic site. Catalysts comprising both an acidic site and a basic site will be referred to herein as multi-functional catalysts. In some or other embodiments, a catalyst used for mediating a condensation reaction may comprise one or more metal atoms. Any of the condensation catalysts may also optionally be disposed on a solid support, if desired.

In some embodiments, the condensation catalyst may comprise a basic catalyst comprising Li, Na, K, Cs, B, Rb, Mg, Ca, Sr, Si, Ba, Al, Zn, Ce, La, Y, Sc, Y, Zr, Ti, hydrotalcite, zinc-aluminate, phosphate, base-treated aluminosilicate zeolite, a basic resin, basic nitride, alloys or any combination thereof. In some embodiments, the basic catalyst may also comprise an oxide of Ti, Zr, V, Nb, Ta, Mo, Cr, W, Mn, Re, Al, Ga, In, Co, Ni, Si, Cu, Zn, Sn, Cd, Mg, P, Fe, or any combination thereof. In some embodiments, the basic catalyst may comprise a mixed-oxide basic catalyst. Suitable mixed-oxide basic catalysts may comprise, for example, Si—Mg—O, Mg—Ti—O, Y—Mg—O, Y—Zr—O, Ti—Zr—O, Ce—Zr—O, Ce—Mg—O, Ca—Zr—O, La—Zr—O, B—Zr—O, La—Ti—O, B—Ti—O, and any combination thereof. In some embodiments, the condensation catalyst may further include a metal or alloys comprising metals such as, for example, Cu, Ag, Au, Pt, Ni, Fe, Co, Ru, Zn, Cd, Ga, In, Rh, Pd, Ir, Re, Mn, Cr, Mo, W, Sn, Bi, Pb, Os, alloys and combinations thereof. Use of metals in the condensation catalyst may be desirable when a dehydrogenation reaction is to be carried out in concert with the condensation reaction. Basic resins may include resins that exhibit basic functionality. The basic catalyst may be self-supporting or adhered to a support containing a material such as, for example, carbon, silica, alumina, zirconia, titania, vanadia, ceria, nitride, boron nitride, a heteropolyacid, alloys and mixtures thereof.

In some embodiments, the condensation catalyst may comprise a hydrotalcite material derived from a combination of MgO and $Al_2O_3$. In some embodiments, the condensation catalyst may comprise a zinc aluminate spinel formed from a combination of ZnO and $Al_2O_3$. In still other embodiments, the condensation catalyst may comprise a combination of ZnO, $Al_2O_3$, and CuO. Each of these materials may also contain an additional metal or alloy, including those more generally referenced above for basic condensation catalysts. In more particular embodiments, the additional metal or alloy may comprise a Group 10 metal such Pd, Pt, or any combination thereof.

In some embodiments, the condensation catalyst may comprise a basic catalyst comprising a metal oxide containing, for example, Cu, Ni, Zn, V, Zr, or any mixture thereof. In some or other embodiments, the condensation catalyst may comprise a zinc aluminate containing, for example, Pt, Pd, Cu, Ni, or any mixture thereof.

In some embodiments, the condensation catalyst may comprise a multi-functional catalyst having both an acidic functionality and a basic functionality. Such condensation catalysts may comprise a hydrotalcite, a zinc-aluminate, a phosphate, Li, Na, K, Cs, B, Rb, Mg, Si, Ca, Sr, Ba, Al, Ce, La, Sc, Y, Zr, Ti, Zn, Cr, or any combination thereof. In further embodiments, the multi-functional catalyst may also include one or more oxides from the group of Ti, Zr, V, Nb, Ta, Mo, Cr, W, Mn, Re, Al, Ga, In, Fe, Co, Ir, Ni, Si, Cu, Zn, Sn, Cd, P, and any combination thereof. In some embodiments, the multi-functional catalyst may include a metal such as, for example, Cu, Ag, Au, Pt, Ni, Fe, Co, Ru, Zn, Cd, Ga, In, Rh, Pd, Ir, Re, Mn, Cr, Mo, W, Sn, Os, alloys or combinations thereof. The basic catalyst may be self-supporting or adhered to a support containing a material such as, for example, carbon, silica, alumina, zirconia, titania, vanadia, ceria, nitride, boron nitride, a heteropolyacid, alloys and mixtures thereof.

In some embodiments, the condensation catalyst may comprise a metal oxide containing Pd, Pt, Cu or Ni. In still other embodiments, the condensation catalyst may comprise an aluminate or a zirconium metal oxide containing Mg and Cu, Pt, Pd or Ni. In still other embodiments, a multi-functional catalyst may comprise a hydroxyapatite (HAP) combined with one or more of the above metals.

In some embodiments, the condensation catalyst may also include a zeolite and other microporous supports that contain Group IA compounds, such as Li, Na, K, Cs and Rb. Preferably, the Group IA material may be present in an amount less than that required to neutralize the acidic nature of the support. A metal function may also be provided by the addition of group VIIIB metals, or Cu, Ga, In, Zn or Sn. In some embodiments, the condensation catalyst may be derived from the combination of MgO and $Al_2O_3$ to form a hydrotalcite material. Another condensation catalyst may comprise a combination of MgO and $ZrO_2$, or a combination of ZnO and $Al_2O_3$. Each of these materials may also contain an additional metal function provided by copper or a Group VIIIB metal, such as Ni, Pd, Pt, or combinations of the foregoing.

The condensation reaction mediated by the condensation catalyst may be carried out in any reactor of suitable design, including continuous-flow, batch, semi-batch or multi-system reactors, without limitation as to design, size, geometry, flow rates, and the like. The reactor system may also use a fluidized catalytic bed system, a swing bed system, fixed bed system, a moving bed system, or a combination of the above. In some embodiments, bi-phasic (e.g., liquid-liquid) and tri-phasic (e.g., liquid-liquid-solid) reactors may be used to carry out the condensation reaction.

In some embodiments, an acid catalyst may be used to optionally dehydrate at least a portion of the reaction product. Suitable acid catalysts for use in the dehydration reaction may include, but are not limited to, mineral acids (e.g., HCl, $H_2SO_4$), solid acids (e.g., zeolites, ion-exchange resins) and acid salts (e.g., $LaCl_3$). Additional acid catalysts may include, without limitation, zeolites, carbides, nitrides, zirconia, alumina, silica, aluminosilicates, phosphates, titanium oxides, zinc oxides, vanadium oxides, lanthanum oxides, yttrium oxides, scandium oxides, magnesium oxides, cerium oxides, barium oxides, calcium oxides, hydroxides, heteropolyacids, inorganic acids, acid modified resins, base modified resins, and any combination thereof. In some embodiments, the dehydration catalyst may also include a modifier. Suitable modifiers may include, for example, La, Y, Sc, P, B, Bi, Li, Na, K, Rb, Cs, Mg, Ca, Sr, Ba, and any combination thereof. The modifiers may be useful, inter alia, to carry out a concerted hydrogenation/dehydrogenation reaction with the dehydration reaction. In some embodiments, the dehydration catalyst may also include a metal. Suitable metals may include, for example, Cu, Ag, Au, Pt, Ni, Fe, Co, Ru, Zn, Cd, Ga, In, Rh, Pd, Ir, Re, Mn, Cr, Mo, W, Sn, Os, alloys, and any combination thereof. The dehydration catalyst may be self-supporting, supported on an inert support or resin, or it may be dissolved in a fluid.

Various operations may optionally be performed on the alcoholic component prior to conducting a condensation reaction. In addition, various operations may optionally be performed on a fluid phase containing the alcoholic component, thereby further transforming the alcoholic component or placing the alcoholic component in a form more suitable for taking part in a condensation reaction. These optional operations are now described in more detail below.

As described above, one or more liquid phases may be present when digesting cellulosic biomass solids. Particularly when cellulosic biomass solids are fed continuously or semi-continuously to the hydrothermal (hydrocatalytic) digestion unit, digestion of the cellulosic biomass solids may produce multiple liquid phases in the hydrothermal digestion unit. The liquid phases may be immiscible with one another, or they may be at least partially miscible with one another. In some embodiments, the one or more liquid phases may comprise a phenolics liquid phase comprising lignin or a product formed therefrom, an aqueous phase comprising the alcoholic component, a light organics phase, or any combination thereof. The alcoholic component being produced from the cellulosic biomass solids may be partitioned between the one or more liquid phases, or the alcoholic component may be located substantially in a single liquid phase. For example, the alcoholic component being produced from the cellulosic biomass solids may be located predominantly in an aqueous phase (e.g., an aqueous phase digestion solvent), although minor amounts of the alcoholic component may be partitioned to the phenolics liquid phase or a light organics phase. In various embodiments, the slurry catalyst may accumulate in the phenolics liquid phase as it forms, thereby complicating the return of the slurry catalyst to the cellulosic biomass solids in the manner described above. Alternative configurations for distributing slurry catalyst particulates in the cellulosic biomass solids when excessive catalyst accumulation in the phenolics liquid phase has occurred are described hereinafter.

Accumulation of the slurry catalyst in the phenolics liquid phase may, in some embodiments, be addressed by conveying this phase and the accumulated slurry catalyst therein to the same location where a fluid phase digestion medium is being contacted with cellulosic biomass solids. The fluid phase digestion medium and the phenolics liquid phase may be conveyed to the cellulosic biomass solids together or separately. Thusly, either the fluid phase digestion medium and/or the phenolics liquid phase may motively return the slurry catalyst back to the cellulosic biomass solids such that continued stabilization of soluble carbohydrates may take place. In some embodiments, at least a portion of the lignin in the phenolics liquid phase may be depolymerized before or while conveying the phenolics liquid phase for redistribution of the slurry catalyst. At least partial depolymerization of the lignin in the phenolics liquid phase may reduce the viscosity of this phase and make it easier to convey. Lignin depolymerization may take place chemically by hydrolyzing the lignin (e.g., with a base) or thermally by heating the lignin to a temperature of at least 250° C. in the presence of molecular hydrogen and the slurry catalyst. Further details regarding lignin depolymerization and the use of viscosity monitoring as a means of process control are described in commonly owned United States Patent Application Publication US20140117275.

After forming the alcoholic component from the cellulosic biomass solids, at least a portion of the alcoholic component may be separated from the cellulosic biomass solids and further processed by performing a condensation reaction thereon, as generally described above. Processing of the alcoholic component that has partitioned between various liquid phases may take place with the phases separated from one another, or with the liquid phases mixed together. For example, in some embodiments, the alcoholic component in a fluid phase digestion medium may be processed separately from a light organics phase. In other embodiments, the light organics phase may be processed concurrently with the fluid phase digestion medium.

Optionally, the fluid phase digestion medium containing the alcoholic component may be subjected to a second catalytic reduction reaction external to the cellulosic biomass solids, if needed, for example, to increase the amount of soluble carbohydrates that are converted into the alcoholic component and/or to further reduce the degree of oxygenation of the alcoholic components that are formed. For example, in some embodiments, a glycol or more highly oxygenated alcohol may be transformed into a monohydric alcohol by performing a second catalytic reduction reaction. The choice of whether to perform a condensation reaction on a monohydric alcohol or a glycol may be based on a number of factors, as discussed in more detail below, and each approach may present particular advantages.

In some embodiments, a glycol produced from the cellulosic biomass solids may be fed to the condensation catalyst. Although glycols may be prone to coking when used in conjunction with condensation catalysts, particularly zeolite catalysts, the present inventors found the degree of coking to be manageable in the production of higher molecular weight compounds. Approaches for producing glycols from cellulosic biomass solids and feeding the glycols to a condensation catalyst are described in commonly owned United States Patent Application Publication US20140121420.

In some embodiments, a phenolics liquid phase formed from the cellulosic biomass solids may be further processed. Processing of the phenolics liquid phase may facilitate the catalytic reduction reaction being performed to stabilize soluble carbohydrates. In addition, further processing of the phenolics liquid phase may be coupled with the production of dried glycols or dried monohydric alcohols for feeding to a condensation catalyst. Moreover, further processing of the phenolics liquid phase may produce methanol and phenolic compounds from degradation of the lignin present in the cellulosic biomass solids, thereby increasing the overall weight percentage of the cellulosic biomass solids that may be transformed into useful materials. Finally, further processing of the phenolics liquid phase may improve the lifetime of the slurry catalyst.

Various techniques for processing a phenolics liquid phase produced from cellulosic biomass solids are described in commonly owned United States Patent Application Publications US2014012141, US20140117277, and US20140121418. As described therein, in some embodiments, the viscosity of the phenolics liquid phase may be reduced in order to facilitate conveyance or handling of the phenolics liquid phase. As further described therein, deviscosification of the phenolics liquid phase may take place by chemically hydrolyzing the lignin and/or heating the phenolics liquid phase in the presence of molecular hydrogen (i.e., hydrotreating) to depolymerize at least a portion of the lignin present therein in the presence of accumulated slurry catalyst. Deviscosification of the phenolics liquid phase may take place before or after separation of the phenolics liquid phase from one or more of the other liquid phases present, and thermal deviscosification may be coupled to the reaction or series of reactions used to produce the alcoholic component from the cellulosic biomass solids. Moreover, after deviscosification of the phenolics liquid phase, the slurry catalyst may be removed therefrom. The catalyst may then be regenerated, returned to the cellulosic biomass solids, or any combination thereof.

In some embodiments, heating of the cellulosic biomass solids and the fluid phase digestion medium to form soluble carbohydrates and a phenolics liquid phase may take place while the cellulosic biomass solids are in a pressurized state. As used herein, the term "pressurized state" refers to a pressure that is greater than atmospheric pressure (1 bar). Heating a fluid phase digestion medium in a pressurized state may allow the normal boiling point of the digestion solvent to be exceeded, thereby allowing the rate of hydrothermal digestion to be increased relative to lower temperature digestion processes. In some embodiments, heating the cellulosic biomass solids and the fluid phase digestion medium may take place at a pressure of at least 30 bar. In some embodiments, heating the cellulosic biomass solids and the fluid phase digestion medium may take place at a pressure of at least 60 bar, or at a pressure of at least 90 bar. In some embodiments, heating the cellulosic biomass solids and the fluid phase digestion medium may take place at a pressure ranging between 30 bar and 430 bar. In some embodiments, heating the cellulosic biomass solids and the fluid phase digestion medium may take place at a pressure ranging between 50 bar and 330 bar, or at a pressure ranging between 70 bar and 130 bar, or at a pressure ranging between 30 bar and 130 bar.

To facilitate a better understanding of the present invention, the following examples of preferred embodiments are given. In no way should the following examples be read to limit, or to define, the scope of the invention.

ILLUSTRATIVE EMBODIMENTS

Examples 1-3

Drying of Wood Chips

Southeastern US pine wood of nominal 58-60% moisture content was ground to a dimension of approximately 8-mm× 3-mm×3-mm using a "Retsch Grinder" Model SM100 rotating knife blade grinder. 2.697 grams of the ground chips were place in a vacuum oven operated at an absolute pressure of 100 Torr, and a temperature of 60° C. A slow $N_2$ purge was added to the vacuum oven (10-20 ml/min) to facilitate water removal.

The wood sample was reweighed periodically to assess moisture content. The initial moisture content was reduced from 58.6% to 34.3% after 40 minutes, and to 13.4% after 58 minutes. By 110 minutes, moisture content was less than 0.5%, as confirmed by overnight drying.

The experiment was repeated with 3.61 grams of wood at an initial moisture content of 53.3%. Moisture content was reduced to 25.2% after 40 minutes, and 11.8% after 58 minutes.

A larger batch of ground pine wood (29 grams) was subsequently dried to a moisture content of 12%, and stored in a sealed bag for use in digestion-reaction experiments.

Example 4

Steaming of Wood to Fully Saturate

Samples of ground pine wood which had dried in air to 34% moisture, were steamed in a food steamer (Oster) for 1 hour. The ground wood was rolled in a paper towel to remove surface moisture, and dried in a vacuum oven overnight to assess moisture content at full saturation. 54% moisture was determined.

Example 5

Digestion and Reaction of Wet Pine Wood (Nominal 54% Moisture)

A 100-ml Parr reactor was charged with a 24.76 grams reaction solvent mixture comprising equal proportions of tetrahydrofurfural alcohol, methyoxypropylphenol, 2-pentanol, cyclohexanone, ethanol, ethylene glycol, propylene glycol, and glycerol, with 2.7 wt % deionized water. The reactor was then charged 013 grams of KOH buffer, and with 1.8 grams of nickel-oxide promoted cobalt molybdate catalyst (DC-2534, containing 1-10% cobalt oxide and molybdenum trioxide (up to 30 wt %) on alumina, and less than 2% nickel), obtained from Criterion Catalyst & Technologies L.P., and sulfided by the method described in US20100236988 Example 5. 3.4 grams of the pine wood of nominal 54% moisture, were charged. Nominal 35 bar of hydrogen was added, and the reactor was heated to 190° C. for 1 hour before ramping over 15 minutes to a temperature of 250° C. for 3 hours, giving a total cycle time of 4 hours.

The cycles were repeated with addition of 3.4 3.83, 4.55, 5.05, 5.63, and 6.5 grams of pine wood at 54% moisture. Final concentration of components derived from dry wood was 24.8 wt %, and nominal final water content was 31.8% for the digestion liquor. All the wood was digested.

The reactor contents were analyzed by gas chromatography using a 60-m×0.32 mm ID DB-5 column of 1 μm thickness, with 50:1 split ratio, 2 ml/min helium flow, and column oven at 40° C. for 8 minutes, followed by ramp to 285° C. at 10° C./min, and a hold time of 53.5 minutes. The injector temperature was set at 250° C., and the detector temperature was set at 300° C. In addition to the initial solvent, a range of alkanes, ketone and aldehyde monooxygenates as well as glycol solvents and products, and polyols (glycerol) were observed, with volatility greater than $C_6$ sugar alcohol sorbitol.

Example 6

Digestion and Reaction of Pine Chips Dried to Nominal 12% Moisture

Example 5 was repeated with addition of wood from Example 3 dried to a nominal 12% moisture. Wood additions entailed 2.78, 2.61, 2.33, 2.99, 2.74, and 2.85 grams, with 24.71 grams of initial solvent. Nominal water content of the reaction mixture increased from 2.7 wt % to 7.5 wt %. Final concentration of components derived from wood was 35 wt %. All wood was digested. GC analysis indicated product formation similar to that observed in Example 4.

Example 6 shows that wood dried to less than 15% moisture can digest within the time allotted for digestion of fully saturated wood exhibiting a moisture content of greater than 50%. Low water content wood can be fed to a solvent mixture maintained at low moisture content (less than 10 wt %), yet still digested to produce intermediate monoxygenates, alkanes, and diols suitable for processing to liquid fuels e.g. via a subsequent acid condensation step.

Example 7

Digestion and Reaction of Chips Dried to Less than 10% Moisture

Example 6 was repeated in a larger 450-ml reactor, with use of a solvent mixture of equal parts methoxypropyl phenol, ethylene glycol, propylene glycol, and tetrahydrofurfural alcohol, with 20% by weight of deionized water. Wood at 8.4% moisture was fed for 6 cycles, with complete dissolution within 5 hours of total reaction time for cycles entailing 1 hour at 190° C., followed by 4 hours at 250° C. This example shows that wood predried to less than 10% moisture can be digested within a reaction time of about 5 hours, in a solvent containing less than 25 wt % water.

Example 8

Multieffect Evaporation

A process simulation was conducted using a commercial process simulator (Aspentech) for drying of a composition of 2.1 wt % ethanol, 17.0 wt % 1,3-propylene glycol in water. The stream initially present at 356 K a pressure greater than 30 bar, was pre-heated to 471 K before flashing by reducing the pressure to 13.7 bar. The bottoms from the flasher contained 27 wt % propylene glycol and only 0.5 wt % ethanol. Heat from the overheaded tops vapour stream at 433 K was extracted in a second flasher operated at 385 K and 1.5 bar, which enabled further removal of water to produce a bottoms stream with 94% propylene glycol and 6% water.

Use of the two "effects" or stages reduced the amount of energy required to dry the glycol stream to 6% water, by 46% relative to the calculated energy required to dry the diol stream to the same weigh percent water in a single flasher. Less than 6% of the glycol present in the feed to the drying system was flashed into the overhead water and ethanol vapour stream.

Thermal stability tests of the propylene glycol, ethanol, and water mixture were conducted in a batch autoclave reactor, to show that the components did not decompose or react measurably when heated to 471 K.

This example shows the energy savings afforded by a two stage multieffect evaporation sequence. Because the initial process stream is available a pressure sufficient to produce and overhead vapour stream comprising water vapour or steam at greater than greater than 13 bar, a common pressure for medium pressure utility steam, and because the components were thermally stable at this pressure, energy required for the second stage flasher could be supplied by the overhead vapour from the first flasher. Net energy savings is approximately 1/N where N is the number of flasher stages or "effects."

Example 9

Condensation Reaction

A reaction mixture composed of 70% water, 26% monooxygenates and 4% deoxygenates was fed to a tube reactor containing ZSM-5 zeolite at 375° C. and 50 psig $N_2$ for a period of 30 days. During this time 10 coke burns were periodically conducted to regenerate catalyst activity lost to coke deposition. The same reaction mixture was fed to a tube reactor containing ZSM-5 zeolite at 375° C. and 50 psig $H_2$ for 30 days. During this time, only 5 coke burns were needed to restore activity lost to coke formation. Overall permanent activity loss was nearly identical between these two experiments suggesting that the coke burns were not the primary cause of permanent catalyst damage, rather simple time on stream exposed to high partial pressure steam had a greater impact. Steam exposure resulting from high water concentrations is thus implicated in activity loss for acid condensation catalysts.

The invention claimed is:

1. A method for thermo-catalytically producing $C_{4+}$ hydrocarbons from lignocellulosic biomass solids comprising:
   a) providing a wet cellulosic biomass solids containing at least 30 wt % water;
   b) contacting the wet cellulosic biomass solids in a drying unit with a high boiling at least partially hydrophilic organic solvent, having a boiling point above 100° C. atmospheric pressure, containing at least one of ethylene glycol, propylene glycol, diols, monooxygenates greater than $C_4$, tetrahydrofurfuryl alcohol, substituted phenol, or a mixture thereof and having a water content of less than 20 wt % water before said contact, at a temperature in the range of from 5° C. to 60° C. and a pressure in the range of from atmospheric pressure to 10,000 kPa producing a low water-content cellulosic biomass solids containing at most 25 wt % water and wet organic solvent;
   c) contacting said low water-content lignocellulosic biomass solids in a hydrothermal digestion unit in the presence of a digestive solvent, hydrogen, and a catalyst capable of activating molecular hydrogen, thereby at least partially transforming said lignocellulosic biomass solids into a reaction product comprising one or more monooxygenates, glycols, diols, monooxygenates greater than $C_4$, tetrahydrofurfuryl alcohol (THFA), and/or phenols in the liquor phase in the hydrothermal digestion unit and producing a product stream comprising the liquor phase and lignin residue;
   d) flashing at least a portion of the product stream at a pressure of at most 5000 kPa and a temperature in the range of from 100° C. to 250° C. thereby separating a light mono-oxygenate stream and producing a heavy stream comprising glycols, diols, monooxygenates greater than $C_4$, THFA, phenols and lignin residue;
   e) separating a high boiling at least partially hydrophilic organic solvent stream from the heavy stream and recycling to the drying unit in step b;

f) removing at least a portion of water from the wet organic solvent producing a dried organic solvent;

g) recycling at least a portion of the dried organic solvent to the drying unit in step b as high boiling at least partially hydrophilic organic solvent; and h) contacting at least a portion of the light mono-oxygenate stream and/or at least a portion of the high boiling least partially hydrophilic organic solvent stream with a condensation catalyst to produce a condensation product stream containing $\geq C_{4+}$ hydrocarbons.

2. The process of claim 1 wherein the water in step f is removed by multi-effect evaporators.

3. The process of claim 1 wherein the water in step f is removed by membrane separation.

4. The process of claim 2 wherein the multi-effect evaporators contains a sequence of vessels each held at a lower pressure than the last.

5. The process of claim 4 wherein the multi-effect evaporators contains at least 2 vessels.

6. The process of claim 5 wherein the multi-effect evaporators contains at least 3 vessels.

7. The process of claim 1 wherein the lignocellulosic biomass solids is contacted with an aqueous solution at a temperature in the range of 0° C. to 60° C. thereby producing a wet cellulosic biomass solids.

8. The process of claim 2 wherein the lignocellulosic biomass solids is contacted with an aqueous solution at a temperature in the range of 0° C. to 60° C. thereby producing a wet cellulosic biomass solids.

9. The process of claim 1 wherein the vapor pressure of the hydrocatalytic digestion unit is at least 100 psi less than without water removal step b.

10. The process of claim 2 wherein the vapor pressure of the hydrocatalytic digestion unit is at least 100 psi less than without water removal step.

11. The process of claim 1 wherein the water content of the high boiling at least partially hydrophilic organic solvent is reduced before water removal step b.

12. The process of claim 1 wherein at least a portion of the lignin residue is removed from the high boiling at least partially hydrophilic organic solvent stream before recycling.

13. The process of claim 1 where the low water-content cellulosic biomass solids contains at most 20 wt % water.

14. The process of claim 13 wherein the wet cellulosic biomass solids contains at least 35 wt % water.

* * * * *